United States Patent [19]
Viera et al.

[11] Patent Number: 5,876,356
[45] Date of Patent: Mar. 2, 1999

[54] SUPERELASTIC GUIDEWIRE WITH A SHAPEABLE TIP

[75] Inventors: Fernando M. Viera, Hialeah; Carol J. Barbre, Miami Lakes, both of Fla.

[73] Assignee: Cordis Corporation, Miami, Fla.

[21] Appl. No.: 825,805

[22] Filed: Apr. 2, 1997

[51] Int. Cl.$^6$ ................................................. A61B 5/00
[52] U.S. Cl. ............................................................ 600/585
[58] Field of Search ................................. 600/585, 433, 600/434, 435

[56] References Cited

U.S. PATENT DOCUMENTS

| | | | |
|---|---|---|---|
| 4,538,622 | 9/1985 | Samson et al. | 600/585 |
| 4,545,390 | 10/1985 | Leary | 600/585 |
| 4,619,274 | 10/1986 | Morrison | 600/585 |
| 4,721,117 | 1/1988 | Mar et al. | 600/585 |
| 4,748,986 | 6/1988 | Morrison et al. | 600/585 |
| 4,763,647 | 8/1988 | Gambale | 600/434 |
| 4,787,399 | 11/1988 | Bonello et al. | 600/585 |
| 4,846,186 | 7/1989 | Box et al. | 600/434 |
| 4,936,312 | 6/1990 | Tsukagoshi | 600/562 |
| 4,971,490 | 11/1990 | Hawkins | 600/585 |
| 5,065,769 | 11/1991 | de Toledo | 600/585 |
| 5,069,226 | 12/1991 | Yamauchi et al. | 600/585 |
| 5,238,005 | 8/1993 | Imran | 600/585 |
| 5,267,573 | 12/1993 | Evans et al. | 600/585 |
| 5,341,818 | 8/1994 | Abrams et al. | 600/585 |
| 5,368,049 | 11/1994 | Ramson et al. | 600/585 |
| 5,372,144 | 12/1994 | Mortier et al. | 600/434 |
| 5,406,960 | 4/1995 | Corso, Jr. | 600/585 |
| 5,745,071 | 5/1998 | Noone | 600/585 |
| 5,749,837 | 5/1998 | Palermo et al. | 600/585 |
| 5,769,796 | 6/1998 | Palermo et al. | 600/585 |

*Primary Examiner*—Max Hindenburg
*Assistant Examiner*—Charles Marmor, II
*Attorney, Agent, or Firm*—Dean L. Garner

[57] ABSTRACT

In accordance with the present invention there is provided a guidewire for navigating through the human vasculature. The guidewire has a distal end for insertion into the body, and a proximal end. The guidewire is made from a core wire formed from a superelastic material and has distal and proximal ends. The core wire has a bore or notch adjacent its distal end, and the bore has a predetermined size and shape. The guidewire further includes a member formed from a malleable material. The member has the same size and shape as the bore or notch and is inserted within the bore or notch. Whereby, after the member is bent, the shape of the distal end of the core wire changes without elastically returning to its original shape. Lastly, the guidewire includes a cover which surrounds the member and portions of the core wire immediately adjacent thereto.

20 Claims, 2 Drawing Sheets

SUPERELASTIC GUIDEWIRE WITH A SHAPEABLE TIP

FIELD OF THE INVENTION

The present invention relates to guidewires for navigating through the human vasculature. The present invention has even further relation to such guidewires used for delivering medical devices, such as balloon catheters, to a target site with the vasculature. The present invention has even further relation to such guidewires made from superelastic materials.

BACKGROUND OF THE INVENTION

Percutaneous transluminal coronary angioplasty (PTCA) is a therapeutic medical procedure used to increase blood flow through the coronary artery and can often be used as an alternative to coronary by-pass surgery. An elongated catheter having a deflated balloon at its distal end is guided through a patient's cardiovascular system to the coronary artery of the heart. The balloon is inflated to compress deposits that have accumulated along the inner walls of the coronary artery to widen the artery lumen and increase blood flow. Typically, the balloon catheter is guided to the specific area within the vessel by an elongated guidewire. The guidewire is inserted into the patient and routed through the cardiovascular system and can be viewed on an x-ray imaging screen.

The path the guidewire follows during this procedure is often tortuous. The distal tip of the guidewire is flexible to avoid damaging the inner walls of the blood vessels which the guidewire tip contacts along the tortuous path. The distal tip is often pre-bent to a desired configuration so that the guidewire can be inserted into branching blood vessels along its path. The physician must be able to orient the tip so it can be pushed into these branching blood vessels. Examples of prior art guidewires are shown in U.S. Pat. No. 4,846,186 issued to Box et al. on Jul. 11, 1989 and U.S. Pat. No. 5,267,574 issued to Viera et al. on Dec. 7, 1993, both of which are hereby incorporated herein by reference.

Such guidewires typically have a core made from stainless steel or the like and coated with a lubricity enhancing agent, such as Teflon®. The distal end of the guidewire is often not coated as such and usually comprises one or two tapered portions which reduce the diameter of the core wire at its distal end. The distal most portion of the core wire is then flattened to form a ribbon tip which makes it easier for a physician to form it into a desired shape. A flexible coiled wire spring surrounds the distal tip of the core wire and is attached thereto. The coil separates from the core wire for a predetermined length and is attached proximal to the flattened distal portion of the core wire.

Among the difficulties sometimes encountered with conventional guidewires, is the possibility that the distal end of the guidewire may kink as it is advanced through the patient's vasculature. Kinking is the result of a plastic deformation of the guidewire and usually is characterized by a sharp deformation or point bend of the very distal section of the wire. Such a deformation may result from attempting to pass a guidewire through a relatively hard, calcified lesion, a mostly occluded vessel section or a very tortuous vascular section. The wire may kink or bend back upon itself in a condition referred to as prolapse. Thereafter, the wire may return to its original shape, or it may remain permanently deformed if, during the bending, the wire material is bent beyond its elastic limit.

Once permanent kinking occurs, the guidewire is usually discarded because it cannot be adequately straightened for use. Consequently, the procedure may have to be aborted and a new guidewire selected, reinserted, and again manipulated and advanced to the target site. Reinsertion of another guidewire increases the risk of trauma to the blood vessels. Unless great care is taken, the blood vessels can be seriously damaged.

Recently, guidewires having core wires which are made from superelastic alloys such as Nitinol® have become more popular. An example of such a wire is given in U.S. Pat. No. 5,411,476 issued to Abrams et al. on May 2, 1995, which is hereby incorporated herein by reference. The superelastic nature of the core wire allows the metal to be deformed and restrained in the deformed condition, causing the alloy to transform from an austenite phase to a martensite phase. However, once the restraint on the superelastic member is removed, the stress is reduced and the core returns to its original undeformed shape by the transformation back to the original phase.

However, as mentioned above it is desirable to provide a guidewire having a curvature or some other shape at its distal end to assist the physician in introducing, advancing and steering the guidewire and catheter to the target site in the blood vessel. One problem with guidewires made of superelastic materials is that, unlike the conventional prior guidewires, they cannot be readily formed, immediately prior to the procedure, into a shape desired for a specific procedure. This is because the superelastic property which is so desirable in prevention of kinking serves to preclude formability by the physician. Accordingly, there is a need for a guidewire that combines the advantages of guidewires formed of superelastic alloys with the ability to form or shape the distal end of the guidewire immediately prior to use by the physician.

Prior art solutions to this problem have included using a malleable safety wire extending between the tip of the core to the extreme distal end of the guidewire. Others have suggested coating the distal end of the guidewire with a malleable material. Examples of such guidewires are presented in U.S. Pat. No. 5,368,049 issued to Raman et al. on Nov. 29, 1994, which is hereby incorporated herein by reference. However, many superelastic materials, such as Ni—Ti alloys, do not weld very well, especially to malleable materials such as stainless steel. This could cause the safety wire mentioned above to detach from the core wire, possibly posing a danger to the patient. In addition, the poor welding properties of such materials make the coating suggestion impractical for manufacturing.

There has, therefore, been a need to have a superelastic guidewire with a shapeable tip which can be better manufactured and is of a simpler design. The present inventions provides such a guidewire and overcomes the shortcomings of the prior art.

SUMMARY OF THE INVENTION

In accordance with the present invention there is provided a guidewire for navigating through the human vasculature. The guidewire has a distal end for insertion into the body, and a proximal end. The guidewire is made from a core wire formed from a superelastic material and has distal and proximal ends. The core wire has a bore or notch adjacent its distal end, and the bore or notch has a predetermined size and shape. The guidewire further includes a member formed from a malleable material which is inserted within the bore or notch. Whereby, after the member is bent, the shape of the distal end of the core wire changes without elastically returning to its original shape. Lastly, the guidewire includes a cover which surrounds the member and portions of the core wire immediately adjacent thereto.

BRIEF DESCRIPTION OF THE DRAWINGS

While the specification concludes with claims which particularly point out and distinctly claim the subject matter forming the present invention, it is believed that the invention will be better understood from the following description of the preferred embodiment taken in conjunction with the accompanying drawings wherein:

DETAILED DESCRIPTION OF THE INVENTION

Figure 1:
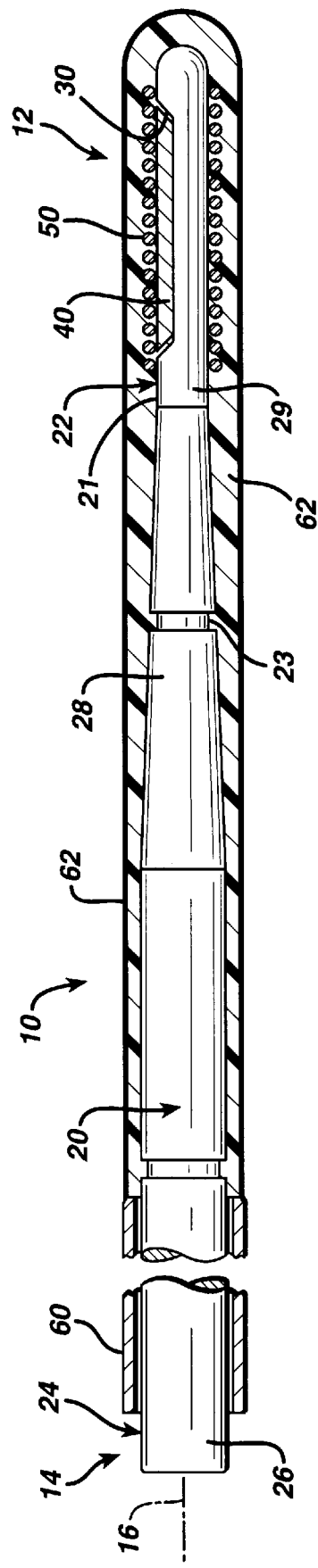
FIG. 1 is a fragmented and sectional illustration of a guidewire in accordance with the present invention, showing the guidewire in a straight position.

Referring to the drawings wherein like numerals indicate the same elements throughout the views, there is shown in FIG. 1 a guidewire 10 in accordance with the present invention. Guidewire 10 has a distal end 12, for insertion into the human vasculature, a proximal end 14, typically used for torquing the guidewire while guiding it through the human body, and a longitudinal axis 16 extending therebetween. Guidewire 10 includes a core wire 20 having a distal end 22 and a proximal end 24. Core wire 20 has a first or proximal uniform diameter portion 26 with a diameter in the range 0.009–0.038 inch, and which extends well over half the length of the guidewire. To improve the depiction of details of the distal portion of the guidewire 10, this uniform diameter elongated portion 26 has been sectioned and a major portion of its length deleted from FIG. 1. The total length of the uniform diameter portion 26 is approximately 148 cm. of the total guidewire length of 180 cm. Distal to portion 26, the core wire has a tapered portion 28 and a second uniform diameter portion 29, distal to portion 28. Distal end 12 could include a hemispherical bead at the extreme distal end, having a slightly larger diameter than the core wire immediately adjacent thereto. Such beads are well known in the art, such as the one disclosed in U.S. Pat. No. 4,538,622 which is hereby incorporated herein by reference.

Core wire 20 is preferably made from a superelastic material. As will be appreciated by those skilled in the art, it is not necessary to have the entire length of the core wire made from a superelastic material. Alternatively, only a predetermined portion of the distal end of the core wire need be made from such a material. An example of such a guidewire is described in U.S. Pat. No. 5,341,818 issued to Abrams et al. on Aug. 30, 1994, which is hereby incorporated herein by reference. Suitable superelastic materials are well known by those skilled in the art, including Nitinol®. That is, the core wire is preferably made of an alloy material comprising about 40 to about 49% titanium and the balance nickel and up to 10% of one or more other alloying elements. The other alloying elements may be selected from the group consisting of iron, cobalt, vanadium and copper. The alloy can contain up to about 10% copper and vanadium and up to 3% of the other alloying elements. The addition of nickel above the equal atomic amounts with titanium and the other identified alloying increase the stress levels at which the stress-induced austenite-to-martensite transformation occurs and ensures that the temperature at which the martensite phase transforms to the austenite phase is well below human body temperature, and preferably below room temperature, so that austenite is in a stable phase throughout a procedure. The excess nickel and additional alloying elements also help to provide an expanded strain range at very high stresses when the stress induced transformation of the austenite phase to the martensite phase occurs.

Guidewire 10 preferably has a means for making the proximal end 24 of the core wire 20 more rigid or stiff than the distal end 22. In FIG. 1, this means is a hypotube 60, covering a predetermined portion of the proximal end of the core wire 30. Preferably, tube 60 is made from a material which has a greater rigidity than the material of the core wire such as stainless steel. This added stiffness helps the doctor torque and guide the guidewire to the target area within a vessel. The guidewire 10 also preferably includes a means for making its distal end 12 more lubricious. In FIG. 1, this is shown as a lubricious coating 62 made from any number materials known in the art including Teflon, any number of polymers including Nylon and Estane, or a hydrophilic coating. The coating could cover only the distal end of the guidewire as shown in FIG. 1, or could cover the entire guidewire. In addition, if a hemispherical bead is present at the extreme distal end of the core wire, the coating may or may not cover it. Core wire 20 includes one or more lateral grooves 23, which create a mechanical lock between coating 62 and core wire 20. Coating 62 preferably fills in the lateral groves. This helps to prevent the Teflon sleeve or coating 62 from sliding with respect to the core wire 20.

Distal end 22 of core wire 20 has a longitudinal bore or notch 30 along its outer surface 21. Bore or notch 30 can be manufactured into the core wire by any method known to those skilled in the art, including grinding and pressing. Bore or notch 30 has a predetermined size, including a predetermined axial height as measured perpendicular to longitudinal axis 16, and a predetermined shape. The axial height and width of the bore preferably ranges from about 0.0005 inch to 0.003 inch and its length along the longitudinal axis preferably ranges from about 0.25 inch to 1 inch.

Guidewire 10 further includes a member 40, formed from a malleable material, such as stainless steel. Member 40 has an axial height which is preferably not substantially greater then the axial height of the bore or notch. This is so the surface of the guidewire is smooth along the bore or notch/member area and ensures that the member does not increase the diameter of the wire at that point. Member 40 is substantially entirely inserted within bore or notch 30. Preferable, member 40 has the same shape as bore or notch 30 and is just slightly smaller than bore or notch 30 so that it fits snugly within bore or notch 30.

Figure 2:
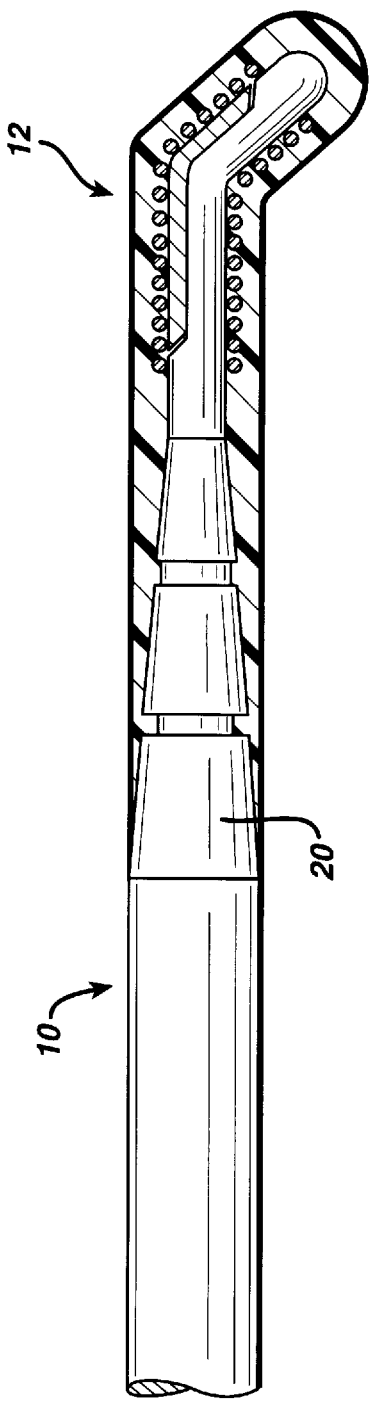
FIG. 2 is a view similar to that of FIG. 1, but showing the guidewire in its bent position.

As seen from FIG. 2, member 40 allows the distal tip 12 of guidewire 10 to be formed into a curvature or some other shape, immediately prior to surgery, to assist the physician in introducing, advancing and steering the guidewire and catheter to the target site in the blood vessel. The physician would simply bend the distal tip 12 of the guidewire, thus bending member 40 as well. The force needed to bend member 40 back to its original position, is greater than elastic force of core wire 20, which wants to return the guidewire to its original position. Therefore, the distal tip 12 of the guidewire can be bent into a desired shape, and remain in that shape during the procedure.

Guidewire 10 further includes a cover 50, which surrounds the member 40 and portions of the core immediately adjacent thereto. FIG. 1 shows the cover 50 as being a coiled spring. Spring 50 can be made from any number of materials known in the art including platinum, which would provide for a radiopaque distal end to the guidewire, or stainless steel. Spring 50 includes a closely packed coils with adjacent coils separated by a spacing or pitch distance of between 0.0005 and 0.002 inches and an optimum or preferred spacing of 0.001 inch. and wherein the wire forming the spring itself has a diameter of 0.002 to 0.003 inches. However, the cover for the guidewire of the present invention need not comprise a spring. In fact, the spring could be removed and the cover could comprise the coating 62 itself.

Cover 50 is preferably tightly wound around the core wire and member, so that it helps retain the member 40 within the bore or notch 30. This is advantageous because it is often not practical to weld or apply an adhesive between materials such as Ni—Ti alloys and stainless steel, as they are often not effective. The cover offers a good solution for keeping the member 40 in the bore or notch, and is economical for manufacturing.

Although particular embodiments of the present invention have been shown and described, modification may be made to the catheter without departing from the spirit and scope of the present invention. The terms used in describing the invention are used in their descriptive sense and not as terms of limitations.

What is claimed is:

1. A guidewire for navigating through the human vasculature, said guidewire having a distal end for insertion into the body, and a proximal end, said guidewire comprising:
   a) a core wire having distal and proximal ends and a longitudinal axis therebetween, said distal end of said core wire is formed from a superelastic material, an outer surface of said core wire having a longitudinal notch at said distal end, said notch having a predetermined size, including an axial height, and shape; and
   b) a member formed from a malleable material, said member having an axial height not substantially greater than said axial height of said notch, said member being substantially entirely inserted within said notch, whereby after said member is bent the shape of said distal end of said core wire changes without elastically returning to its original shape; and
   c) a cover surrounding said member and portions of the core wire immediately adjacent thereto.

2. The guidewire according to claim 1, wherein said member has substantially the same size and shape as said longitudinal notch.

3. The guidewire according to claim 1 wherein said cover comprises a coiled spring.

4. The guidewire according to claim 1 further including a lubricious sleeve covering said distal end of said core wire.

5. The guidewire according to claim 4 wherein said sleeve comprises polytetrafluroethylene.

6. The guidewire according to claim 4 wherein distal end of said core wire includes at least one lateral groove on its outer surface.

7. The guidewire according to claim 1 wherein said cover comprises a polymeric sleeve.

8. The guidewire according to claim 1 wherein said cover comprises a polytetrafluroethylene sleeve.

9. The guidewire according to claim 1 wherein said core wire comprises about 40 to about 49% titanium and the balance of the alloy being nickel and up to 10% of other alloying elements.

10. The guidewire according to claim 9 wherein said other alloying elements are selected from the group comprising of iron, cobalt, vanadium and copper.

11. A guidewire for navigating through the human vasculature, said guidewire having a distal end for insertion into the body, and a proximal end, said guidewire comprising:
    a) a core wire having distal and proximal ends and a longitudinal axis therebetween, said distal end of said core wire is formed from a superelastic material, an outer surface of said core wire having a longitudinal notch at said distal end, said notch having a predetermined size, including an axial height, and shape;
    b) a means for making said proximal end of said core wire more rigid than the distal end;
    c) a member formed from a malleable material, said member having an axial height not substantially greater than said axial height of said notch, said member being substantially entirely inserted within said notch, whereby after said member is bent the shape of said distal end of said core wire changes without elastically returning to its original shape; and
    d) a cover surrounding said member and portions of the core wire immediately adjacent thereto.

12. The guidewire according to claim 11 wherein said means for making said proximal end of said core wire more rigid than said distal end comprises a hypotube covering a predetermined length of said proximal end of said core wire.

13. The guidewire according to claim 12 wherein said hypotube comprises stainless steel.

14. The guidewire according to claim 11, wherein said member has substantially the same size and shape as said longitudinal notch.

15. The guidewire according to claim 11 wherein said cover comprises a coiled spring.

16. The guidewire according to claim 11 further including a lubricious sleeve covering said distal end of said core wire.

17. The guidewire according to claim 16 wherein distal end of said core wire includes at least one lateral groove on its outer surface.

18. The guidewire according to claim 11 wherein said cover comprises a polymeric sleeve.

19. The guidewire according to claim 11 wherein said core wire comprises about 40 to about 49% titanium and the balance of the alloy being nickel and up to 10% of other alloying elements.

20. The guidewire according to claim 19 wherein said other alloying elements are selected from the group comprising of iron, cobalt, vanadium and copper.

* * * * *